(12) United States Patent
Lee et al.

(10) Patent No.: US 7,964,695 B2
(45) Date of Patent: *Jun. 21, 2011

(54) CHAIN EXTENDERS

(75) Inventors: John Y. Lee, Baton Rouge, LA (US); Paul L. Wiggins, Baton Rouge, LA (US); Judit Orgad, Baton Rouge, LA (US); Mahmood Sabahi, Baton Rouge, LA (US); Vernon O. Brandt, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 260 days.

This patent is subject to a terminal disclaimer.

(21) Appl. No.: 11/534,968

(22) Filed: Sep. 25, 2006

(65) Prior Publication Data

US 2007/0270566 A1    Nov. 22, 2007

Related U.S. Application Data

(63) Continuation-in-part of application No. 11/390,777, filed on Mar. 27, 2006, now Pat. No. 7,288,677.

(60) Provisional application No. 60/665,915, filed on Mar. 28, 2005.

(51) Int. Cl.
```
C08G 18/10    (2006.01)
C08G 18/32    (2006.01)
C07C 249/00   (2006.01)
C07C 251/00   (2006.01)
C07C 257/00   (2006.01)
C07C 263/00   (2006.01)
C07C 265/00   (2006.01)
C07C 267/00   (2006.01)
C07C 291/00   (2006.01)
```

(52) U.S. Cl. .............. 528/61; 528/44; 528/59; 552/301; 564/269; 564/271; 564/277

(58) Field of Classification Search ............... 252/182.1; 528/61, 44; 552/301; 564/271
See application file for complete search history.

(56) References Cited

U.S. PATENT DOCUMENTS

| | | |
|---|---|---|
| 2,380,420 A | 7/1945 | Emerson |
| 2,582,128 A | 1/1952 | Hurwitz et al. |
| 2,953,579 A | 9/1960 | Williams et al. |
| 2,965,605 A | 12/1960 | Reynolds et al. |
| 3,209,030 A | 9/1965 | Bicek |
| 3,275,567 A | 9/1966 | Keith et al. |
| 3,336,386 A | 8/1967 | Dovell et al. |
| 3,350,450 A | 10/1967 | Dovell et al. |
| 3,414,616 A | 12/1968 | Summers |
| 3,519,603 A | 7/1970 | Lohse et al. |
| 3,538,161 A | 11/1970 | Dovell |
| 3,609,121 A | 9/1971 | Lohse et al. |
| 3,625,710 A | 12/1971 | Rizzi |
| 3,658,937 A | 4/1972 | Terni et al. |
| 3,761,425 A | 9/1973 | Baessler et al. |
| 3,937,730 A | 2/1976 | Vogel et al. |
| 3,943,158 A | 3/1976 | Dietrich et al. |
| 3,952,056 A | 4/1976 | Vogel et al. |
| 3,994,975 A | 11/1976 | Oude Alink et al. |
| 4,045,486 A | 8/1977 | Krall et al. |
| 4,140,718 A | 2/1979 | Symon |
| 4,161,492 A | 7/1979 | Weissel |
| 4,317,916 A | 3/1982 | Degischer et al. |
| 4,373,107 A | 2/1983 | Tahara et al. |
| 4,520,186 A * | 5/1985 | Hess et al. ............ 528/73 |
| 4,521,624 A | 6/1985 | Jackisch |
| 4,528,363 A | 7/1985 | Tominaga |
| 4,631,298 A | 12/1986 | Presswood |
| 4,663,201 A | 5/1987 | House et al. |
| 4,714,512 A | 12/1987 | House et al. |
| 4,760,183 A | 7/1988 | Papenfuhs et al. |
| 4,789,691 A | 12/1988 | Matzke et al. |
| 4,798,862 A | 1/1989 | Gillis, Jr. |
| 4,806,616 A | 2/1989 | Baumann et al. |
| 4,900,868 A | 2/1990 | Merten et al. |
| 4,925,974 A | 5/1990 | Gras |
| 5,001,267 A | 3/1991 | Speranza et al. |
| 5,002,806 A | 3/1991 | Chung |
| 5,008,453 A * | 4/1991 | Nalepa et al. .......... 564/271 |
| 5,041,668 A | 8/1991 | Nalepa et al. |
| 5,059,672 A | 10/1991 | Engebretson |
| 5,145,825 A | 9/1992 | Deeba et al. |

(Continued)

FOREIGN PATENT DOCUMENTS

CA    1218190 A    2/1987

(Continued)

OTHER PUBLICATIONS

John T. Lai, Ketoform reaction. Synthesis of hindered imines from 2,6-dialkylanilines and ketones, Tetrahedron Letters 43 (2002) 1965-1967, 2002 Elsevier Science Ltd.*

Pamphlate © 2001 Albemarle Corporation, Ethacure and Albemarle are trademarks of Albemarle Corporation http://www.albemarle.com/TDS/Curatives/SC7008F_ETHACURE_100LC.pdf.*

(Continued)

*Primary Examiner* — Ling-Siu Choi
*Assistant Examiner* — Bijan Ahvazi
(74) *Attorney, Agent, or Firm* — James A. Jubinsky

(57) ABSTRACT

This invention provides chain extender compositions. These compositions comprise
(i) an aromatic primary diamine, and
(ii) a component selected from the group consisting of:
  (a) an aliphatic secondary diamine;
  (b) an aliphatic primary diamine;
  (c) an aliphatic secondary diamine and an aliphatic primary diamine;
  (d) a diimine; and
  (e) a combination of any two or more of (a) through (d).

When (ii) is (a), (a) has amino hydrocarbyl groups which are secondary or tertiary hydrocarbyl groups; when (ii) is (d), and (d) is an aromatic diimine, each imino hydrocarbylidene group has at least two carbon atoms. Processes for producing polyurethanes, polyureas, and polyurea-urethanes are also provided.

5 Claims, No Drawings

U.S. PATENT DOCUMENTS

| | | | |
|---|---|---|---|
| 5,312,886 | A | 5/1994 | House et al. |
| 5,430,188 | A | 7/1995 | Bader et al. |
| 5,470,890 | A | 11/1995 | House et al. |
| 5,498,585 | A | 3/1996 | Bartels et al. |
| 5,591,807 | A | 1/1997 | Cai et al. |
| 5,616,799 | A | 4/1997 | Planker et al. |
| 5,646,235 | A | 7/1997 | Zimmerman et al. |
| 5,744,642 | A | 4/1998 | Lantzsch et al. |
| 5,847,067 | A | 12/1998 | Gras |
| 5,859,164 | A | 1/1999 | Gras et al. |
| 5,874,619 | A | 2/1999 | Wiggins et al. |
| 6,013,755 | A | 1/2000 | Primeaux, II et al. |
| 6,103,799 | A | 8/2000 | Lassila et al. |
| 6,156,863 | A | 12/2000 | Wenning |
| 6,218,480 | B1 | 4/2001 | Rappoport |
| 6,399,736 | B1 | 6/2002 | Primeaux, II et al. |
| 6,403,752 | B1 | 6/2002 | House et al. |
| 6,429,338 | B1 | 8/2002 | Burdeniuc et al. |
| 6,444,721 | B2 | 9/2002 | Schwalm et al. |
| 6,803,445 | B2 | 10/2004 | Ishikawa et al. |
| 7,767,858 | B2 | 8/2010 | Wiggins et al. |
| 2002/0028901 | A1* | 3/2002 | Gunatillake et al. ............ 528/28 |
| 2003/0004265 | A1 | 1/2003 | Gupta et al. |
| 2004/0015016 | A1 | 1/2004 | Su et al. |
| 2004/0019238 | A1 | 1/2004 | Su et al. |
| 2004/0054150 | A1 | 3/2004 | Murray |
| 2004/0167311 | A1 | 8/2004 | Slagel et al. |
| 2004/0180778 | A1 | 9/2004 | Small |
| 2007/0066786 | A1 | 3/2007 | Hanson, Jr. |
| 2007/0073030 | A1 | 3/2007 | Wiggins et al. |
| 2008/0194788 | A1 | 8/2008 | Lee et al. |

FOREIGN PATENT DOCUMENTS

| | | |
|---|---|---|
| CN | 1352202 | 6/2002 |
| CN | 1939949 A | 4/2007 |
| DE | 1163315 | 2/1964 |
| DE | 2940738 A1 | 4/1981 |
| DE | 264014 | 1/1989 |
| DE | 3728141 | 3/1989 |
| DE | 19701835 A1 | 7/1998 |
| DE | 102005046641 A1 | 4/2007 |
| EP | 0014985 A1 | 9/1980 |
| EP | 0288067 A1 | 10/1988 |
| EP | 0309980 A1 | 4/1989 |
| EP | 0420426 A2 | 4/1991 |
| EP | 0469751 A1 | 2/1992 |
| EP | 0688802 A1 | 12/1995 |
| EP | 0779278 | 6/1997 |
| EP | 1067116 A1 | 1/2001 |
| EP | 1229020 A1 | 8/2002 |
| EP | 0802209 B1 | 4/2003 |
| GB | 1070759 | 6/1967 |
| GB | 1320863 | 6/1973 |
| GB | 1478446 | 6/1977 |
| JP | 63052146 A2 | 3/1988 |
| JP | 5274914 A2 | 10/1993 |
| JP | 09100260 A | 4/1997 |
| WO | WO-92/18575 A1 | 10/1992 |
| WO | WO-97/01529 | 1/1997 |
| WO | WO-00/26181 A1 | 5/2000 |
| WO | WO-02/102869 A1 | 12/2002 |
| WO | WO 02/102869 A1 * | 12/2002 |
| WO | WO-03/018531 A1 | 3/2003 |
| WO | WO-2004/073634 A2 | 9/2004 |
| WO | WO-2004/092632 A2 | 10/2004 |
| WO | WO-2005/033119 | 4/2005 |
| WO | WO-2006/028728 A1 | 3/2006 |
| WO | WO-2006/104528 A1 | 10/2006 |
| WO | 2007050542 A1 | 5/2007 |

OTHER PUBLICATIONS

Adams et al., "Restricted Rotation in Aryl Amines. XIV. Isopropyl Derivatives of Dibenzenesulfonamidomesitylene", J. Am. Chem. Soc., 1950, pp. 5077-5079, vol. 72.

Barmetter, "Acid-Catalyzed [3.3]-Sigmatropic Rearrangethents of N-Propargylanilines", Helvetica Chimica Acta, 1990, pp. 1515-1573, vol. 73, Verlag Helvetica Chimica Acta, Basel, CH.

Billaud et al., "Quantitative Analysis of Epoxy Resin Cure Reaction: A Study by Near-Infrared Spectroscopy", Applied Spectroscopy, 2002, pp. 1413-1421, vol. 56(11).

Borges-Lopes et al., "Synthesis and Characterization of New Methyl-Substituted Azomethine-Siloxane Liquid Crystal Macrocycles Influence of the Methyl-Substitution on the Cycle Formation", Polymer Bulletin, 1995, pp. 523-530, vol. 34, Springer, Heidelberg, Berlin, DE.

Campbell et al., "The Preparation of Unsymmetrical Secondary Aliphatic Amines",.J. Am. Chem. Soc., 1944, pp. 82-84, vol. 66.

Childs et al., "Assembly of a Nanoscale Chiral Ball Through Supramolecular Aggregation of Bowl-Shaped Triangular Helicates", Angewandte Chemie, 2002, pp. 4244-4247, vol. 41, VCH Verlagsgesellschaft, Weinheim, DE.

Childs et al., "Using Noncovalent Intra-strand and Inter-strand Interactions to Prescribe Helix Formation within a Metallo-supramolecular System", Chem. Eur. J., 2004, pp. 4291-4300, vol. 10(17).

Deschenaux et al., "Structural Isomerism in Polycondensates. IV. Synthesis and Characterization of Liquid Crystalline Poly(azomethines) and Low Molecular Weight Model Compounds", Helvetica Chimica Acta, 1986, pp. 1349-1355, vol. 69(6).

Distefano, "Reinvestigation of the Formaldehyde-Aniline Condensation. Part 4. Ultraviolet Photoelectron and Electron Transmission Spectra of N-Methyleneaniline and its Symmetric Dimethyl Ring-substituted Homologues and Semiempirical Theoretical Evaluations", J. Chem. Soc. Perkin Trans II, 1985, pp. 1623-1627.

Dovell & Greenfield, "Platinum Metal Sulfides as Heterogeneous Hydrogenation Catalysts", J. Am. Chem. Soc., 1965, pp. 2767-2768, vol. 87.

Dvolaitzky et al., "Stable N,N'-di-tert-butyl-meta-phenylenebisnitroxides-Unexpected Ground-State Singlets", Angewandte Chemie Int. Ed. Engl., 1992, pp. 180-181, vol. 31(2).

Emerson et al., "The Reductive Alkylation of Hindred Aromatic Primary Amines", J. Am. Chem. Soc., 1941, pp. 972-974, vol. 63.

Hine et al., "Polar Effects on the Formation of Imines from Isobutyraldehyde and Primary Aliphatic Amines", The Journal of Organic Chemistry, 1970, pp. 340-344, vol. 85.

Jie et al., "Bridged Bis-Pyridinylimino Dinickel (II) Complexes: Syntheses, Characterization, Ethylene Oligomerization and Polymerization", Journal of Organometallic Chemistry, 2005, pp. 1739-1749, vol. 690, Elsevier-Sequoia S.A. Lausanne, CH.

Lai, J.T., "Ketoform Reaction. Synthesis of Hindered Imines from 2,6-dialkylanilines and Ketones", Tetrahedron Letters, 2002, p. 1965-1967; 1996, vol. 43, Elsevier Science Publishers, Amsterdam, NL.

Layer, Robert W.; "The Chemistry of Imines", Chemical Reviews; 1963; vol. 63; pp. 489-510.

Luo et al., "New Bi-nuclear and Multi-nuclear α-dilmine/nickel Catalysts for Ethylene Polymerization", Journal of Molecular Catalysts, 2005, pp. 153-161, vol. 227.

March, "Reactions, Mechanisms, and Structure", Advanced Organic Chemistry, 1992, pp. 896-900, 4$^{th}$ Ed., John Wiley & Sons, US.

Mi et al., "Homo- and Copolymerization of Norbornene and Styrene with Pd- and Ni-Based Novel Bridged Dinuclear Diimine Complexes and MAO",Macromol. Chem. Phys., 2003, pp. 868-876, vol. 204(5/6).

Pal et al., "Schiff Base Linked Ferrocenyl Complexes for Second-Order Nonlinear Optics", Journal of Organometallic Chemistry, 2000, pp. 248-259, vol. 604, Elsevier-Sequoia S.A., Lausanne, CH.

Parker, et al., "Reaction Chemistry of Tri-Substituted Mesitylene derivatives and the Synthesis of Sterically Buttressed 1,3,5-triaminocyclohexyl Ligands", J. Chem. Soc., Perkin Transactions 2, Chemical Society, 1997, pp. 1445-1452.

Patai, The Chemistry of the Carbon-Nitrogen Double Bond, 1970, pp. 61-67, 130, 255-256, 276-293, 296-298, Interscience Publishers, Great Britain.

Perez, Jr. et al., "Performance and Processing Enhancements of Aromatic Polyurea Elastomer Systems Prepared from High 2,4'-MDI Isocyanates", Huntsman Corporation; 3 pages.

Poseyet al., "New Secondary Amine Chain Extenders for Aliphatic Polyurea Materials", Polyurea Development Association 2003

Annual Conference, Aug. 19-21, 2003, John Ascuaga's Nugget Casino Resort, Reno, NV; 11 pages.

Rylander, "Reduction Alkylation", Catalytic Hydrogenation in Organic Syntheses, 1979, pp. 165-174, Academic Press, New York, NY, USA.

Smith et al., "Preparation of Polyimides Utilizing the Diels-Alder Reaction. 1,4-N,N'-Bis(Butadienyl-2-Methyl) Diamido)-2,3,5,6-tetramethylbenzenes with Bismaleimides", Macromolecules, American Chemical Society, 1996, pp. 1123-1130, vol. 29, Easton, US.

Sun et al., "Supramolecular Helical Architecture Assembled by Double-Helical [$Ag_2L_2$] Units", Journal of Organometallic Chemistry, 2004, pp. 43-49, vol. 689.

Taneda et al., "Photochromism of Polymorphic 4, 4'-methylenebis-(N-salicylidene-2, 6-diisopropylaniline) Crystals", Org. Biomol. Chem., 2004, pp. 499-504, vol. 2(4).

Trost et al., "Dehydrogenation of Amines. An approach to Imines and Aldehydes", The Journal of Organic Chemistry, 1981, pp. 4617-4620, vol. 46.

Voigt-Martin et al., "Structure and Defects in Sanidic Liquid Crystalline Polymers. 2. Structure Analysis of Sanidic Polymers by Simulation of Diffraction Patterns From Monomeric Analogs", Macromolecules, 1995, pp. 243-254, vol. 28(1).

CAPLUS Abstract of Vasilenko et al., "Electron Spectra and Structure of Molecules Containing a Carbon:Nitrogen Group. II. Absorption Spectra of Benzyideneaniline Derivatives and Bis(azomethines)", Zhurnal Fizlcheskol Khimii; 1976; 50(3(; pp. 597-601; Accession No. 1976:405028.

CAPLUS Abstract of Zhang et al., "Synthesis of Bis-(salicylaldininato) Nickel Complexes and Their Catalytic Behavior for Vinyl Polymerization of Norbornene"; Gaofenzi Xuebao; 2004; (5); pp. 758-762; Accession No. 2004:985377.

Johnson Matthey Catalysts & Chemicals Division, Heterogeneous Catalyst Application Table.

Arunajatesan, V., et al., "Optimization of Reductive Alkylation Catalysts by Experimental Design", Organic Reactions Catalysis Society, 2003, pp. 1-6.

De, D., et al., "Polyurethanes With a Diamine-Diamide Chain Extender", Polymer Preprints, 2007, 48(1), 485-486.

Luo, Y., et al., "Response Behavior of an Epoxy Resin/Amine Curing Agent/Carbon Black Composite Film to Various Solvents", Materials Science and Engineering B 139 (2007), pp. 105-113.

Mylroie, Victor L., et al., "Reductive Alkylation Optimized by Techniques of Experimental Design", Catalysis of Organic Reactions, Chem. Ind. Series, vol. 68, Marcel Dekker, New York, 1996, pp. 301-312.

Wang et al., "Bolaamphiphilic Single-Chain Bis-Schiff Base Derivatives: Aggregation and Thermal Behavior in Aqueous Solution." Langmuir, 2001, vol. 17, p. 3162-3167.

Arunajatesan, V., et al., "Optimization of Reductive Alkylation Catalysts by Experimental Design", Chemical Industries (CRC Press), vol. 115, Catalysis of Organic Reactions), 2007, pp. 481-487.

* cited by examiner

CHAIN EXTENDERS

REFERENCE TO RELATED APPLICATIONS

This application is a continuation-in-part of U.S. application Ser. No. 11/390,777, filed Mar. 27, 2006, which in turn claims the priority of U.S. Provisional Application No. 60/665,915, filed Mar. 28, 2005, the disclosures of which are incorporated herein by reference.

TECHNICAL FIELD

This invention relates to the use of aromatic diamines to form polyurethanes, polyureas, and polyurea-urethanes.

BACKGROUND

There are many polyfunctional compounds, including diols and aromatic diamines, which are indicated to be useful as chain extenders in the preparation of polyurethane, polyurea, and polyurethane-urea polymers and/or as curing agents for epoxy resins. None of these compounds has a reactivity such as to make it universally ideal, and many fail to provide satisfactory properties in the products made by their use. Thus, there is still a need to find compounds capable of serving as chain extenders or curing agents. U.S. Pat. No. 4,806,616 teaches the use of certain N,N'-dialkylphenylenediamines as chain extenders in preparing polyurethanes and polyureas. In this connection, also see for example U.S. Pat. No. 4,528,363, which teaches the use of secondary aliphatic diamines as part of a resin binder, and U.S. Pat. No. 6,218,480 B1, which discloses use of aromatic diamines as hardeners for polyurethanes. Secondary aromatic diamines have also been used as anti-degradants for rubber; see U.S. Pat. No. 4,900,868.

There is a growing need for chain extenders with slower cure rates, so it would be a further advantage if aromatic diamines exhibited slower curing rates than those of presently available chain extenders.

SUMMARY OF INVENTION

This invention in part provides chain extenders which are mixtures of aromatic primary diamines and one or more other components. These mixtures, when included in formulations for polyurethanes, polyureas, and polyurea-urethanes, produce such polymers at desired cure rates and having desirable physical properties.

One embodiment of this invention provides a chain extender composition. The composition comprises (i) an aromatic primary diamine and (ii) another component. The component is selected from the group consisting of:
  (a) an aliphatic secondary diamine;
  (b) an aliphatic primary diamine;
  (c) an aliphatic secondary diamine and an aliphatic primary diamine;
  (d) a diimine; and
  (e) a combination of any two or more of (a) through (d).
When (ii) is (a), (a) has amino hydrocarbyl groups which are secondary or tertiary hydrocarbyl groups. When (ii) is (d), and (d) is an aromatic diimine, each imino hydrocarbylidene group has at least two carbon atoms.

Another embodiment of this invention is a process for producing a polymer which is a polyurethane, polyurea, or polyurea-urethane. The process comprises mixing together (A) at least one aromatic polyisocyanate, (B) at least one polyol and/or at least one polyetheramine, and (C) a chain extender comprised of (i) an aromatic primary diamine and (ii) another component. The component is selected from the group consisting of:
  (a) an aliphatic secondary diamine;
  (b) an aliphatic primary diamine;
  (c) an aliphatic secondary diamine and an aliphatic primary diamine;
  (d) a diimine; and
  (e) a combination of any two or more of (a) through (d).
When (ii) is (a), (a) has amino hydrocarbyl groups which are secondary or tertiary hydrocarbyl groups. When (ii) is (d), and (d) is an aromatic diimine, each imino hydrocarbylidene group has at least two carbon atoms.

Still another embodiment of this invention is a polymer which is a polyurethane, polyurea, or polyurea-urethane, which polymer is formed from ingredients comprising (A) at least one aromatic isocyanate, (B) at least one polyol and/or at least one polyetheramine, and (C) a chain extender comprised of (i) an aromatic primary diamine and (ii) another component. The component is selected from the group consisting of:
  (a) an aliphatic secondary diamine;
  (b) an aliphatic primary diamine;
  (c) an aliphatic secondary diamine and an aliphatic primary diamine;
  (d) a diimine; and
  (e) a combination of any two or more of (a) through (d).
When (ii) is (a), (a) has amino hydrocarbyl groups which are secondary or tertiary hydrocarbyl groups. When (ii) is (d), and (d) is an aromatic diimine, each imino hydrocarbylidene group has at least two carbon atoms.

These and other embodiments and features of this invention will be still further apparent from the ensuing description and appended claims.

FURTHER DETAILED DESCRIPTION OF THE INVENTION

Chain Extender Compositions of the Invention

Chain extender compositions of this invention are made up of an aromatic primary diamine and one or more other components selected from (a) an aliphatic secondary diamine which has amino hydrocarbyl groups which are secondary or tertiary hydrocarbyl groups; (b) an aliphatic primary diamine; (c) an aliphatic secondary diamine and an aliphatic primary diamine; and (d) a diimine, wherein when said diimine is an aromatic diimine, each imino hydrocarbylidene group has at least two carbon atoms. Preferred components for use with the aromatic primary diamine are aliphatic secondary diamines. The components can be present in the chain extender composition in a variety of proportions; the preferred ratios vary with the type of component from (ii).

I. Component (i)

Aromatic primary diamines are component (i) of the chain extender compositions of the invention.

One type of aromatic primary diamine that can be used in this invention is an aromatic primary diamine in which at least one position ortho to each amino group has a hydrogen atom as a substituent, and which aromatic primary diamine is either in the form of one phenyl ring having two amino groups on the ring or in the form of two phenyl rings connected by an alkylene bridge and having one amino group on each ring. The phenyl rings may have, but need not have, one or more hydrocarbyl groups on the phenyl ring(s). Hydrocarbyl groups, when present on the phenyl rings, may be the same or different. When both amino groups are on one phenyl ring, the amino groups may be in any position relative to each other on the ring; preferably, the amino groups are meta or para relative to each other. When the amino groups are on two phenyl rings connected by an alkylene bridge, they may be in any position on the rings; preferably, each amino group is meta or para relative to the alkylene bridge. The alkylene bridge of the two-ring diamine has from one to about six carbon atoms; preferably, the alkylene bridge has from one to about three carbon atoms. More preferably, the alkylene bridge has one or two carbon atoms; highly preferred is an alkylene bridge having one carbon atom. The hydrocarbyl groups, when present on the phenyl ring(s), are as described above for the aromatic diimines. When one or more hydrocarbyl groups are present on the phenyl ring(s), the hydrocarbyl groups can have from one to about twenty carbon atoms; preferably, the hydrocarbyl groups have from one to about six carbon atoms.

Suitable aromatic primary diamines of this type having both amino groups on one phenyl ring include, but are not limited to, 1,2-benzenediamine, 1,3-benzenediamine, 1,4-benzenediamine, 4-ethyl-1,2-benzenediamine, 2-isopropyl-1,3-benzenediamine, 4-tert-butyl-1,3-benzenediamine, 2-pentyl-1,4-benzenediamine, 4,5-dihexyl-1,2-benzenediamine, 4-methyl-5-heptyl-1,3-benzenediamine, 4,6-di-n-propyl-1,3-benzenediamine, 2,5-dioctyl-1,4-benzenediamine, 2,3-diethyl-1,4-benzenediamine, and 4,5,6-trihexyl-1,3-benzenediamine.

Examples of suitable aromatic primary diamines of this type in which one amino group is on each of two phenyl rings include 2,2'-methylenebis(benzeneamine), 2,3'-methylenebis-(benzeneamine), 2,4'-methylenebis(benzeneamine), 3,3'-methylenebis(benzeneamine), 3,4'-methylenebis(benzeneamine), 4,4'-methylenebis(benzeneamine), 4,4'-(1,2-ethanediyl)bis-(benzeneamine), 3,4'-(1,3-propanediyl)bis(benzeneamine), 2,2'-methylenebis(5-tert-butylbenzeneamine), 3,3'-methylenebis(2-methylbenzeneamine), 3,3'-methylenebis(5-pentylbenzeneamine), 3,3'-methylenebis(6-isopropylbenzeneamine), 4,4'-methylenebis(2-methylbenzeneamine), 4,4'-methylenebis(3-sec-butylbenzeneamine), 4,4'-(1,2-ethanediyl)bis(2-methylbenzeneamine), 3,3'-methylenebis(2,4-dipentylbenzeneamine), 3,3'-methylenebis(5,6-diisopropylbenzeneamine), 4,4'-methylenebis(2,3-di-sec-butylbenzeneamine), 4,4'-methylenebis(3,5-di-tert-butylbenzeneamine), and the like.

Another type of aromatic primary diamine that can be used in this invention, which is a preferred type of aromatic primary diamine, is an aromatic primary diamine in which each position ortho (immediately adjacent) to an amino group bears a hydrocarbyl group, and which aromatic primary diamine either is in the form of one phenyl ring having two amino groups on the ring, which amino groups are meta or para relative to each other, or is in the form of two phenyl rings connected by an alkylene bridge and having one amino group on each ring. The hydrocarbyl groups on the phenyl rings (adjacent to the amino groups) generally have up to about twenty carbon atoms, and the hydrocarbyl groups may be the same or different. The alkylene bridge of the two-ring primary diamine has from one to about six carbon atoms; preferably, the bridge has from one to about three carbon atoms. More preferably, the alkylene bridge has one or two carbon atoms; especially preferred as the alkylene bridge is a methylene group. Particularly preferred hydrocarbyl groups on the phenyl ring(s) are methyl, ethyl, isopropyl, butyl, and mixtures of two or more of these groups. Here, butyl groups include n-butyl, sec-butyl, and t-butyl groups.

More preferred aromatic primary diamines with two amino groups on one phenyl ring have the amino groups meta relative to each other. Highly preferred hydrocarbyl groups are methyl, ethyl, isopropyl, butyl, and mixtures thereof, where the preference for butyl groups includes n-butyl, sec-butyl, and t-butyl groups. Particularly preferred are aromatic primary diamines in which the hydrocarbyl group between the two meta amino groups is a methyl group, while the two remaining hydrocarbyl groups are ethyl groups, and those in which the hydrocarbyl group between the two meta amino groups is an ethyl group, while one of the two remaining hydrocarbyl groups is a methyl group and the other is an ethyl group, and mixtures thereof. More preferred aromatic primary diamines are also those in which one amino group is on each of two phenyl rings, where the two phenyl rings are connected via an alkylene bridge, and have both amino groups para relative to the alkylene bridge. An especially preferred aromatic primary diamine of this type is a compound where each hydrocarbyl group ortho to an amino group is an ethyl group and the alkylene bridge is a methylene group.

A preferred aromatic primary diamine is one in which each position ortho to an amino group bears a hydrocarbyl group, and which aromatic primary diamine is in the form of one phenyl ring having two amino groups on the ring, which amino groups are meta or para relative to each other, and in which the aromatic primary diamine has amino groups are meta relative to each other, and/or the ortho hydrocarbyl groups are methyl, ethyl, isopropyl, butyl, or mixtures thereof.

Examples of more preferred aromatic primary diamines include 3,6-di-n-butyl-1,2-benzenediamine, 2,4,6-triethyl-1,3-benzenediamine, 2,4-diethyl-6-methyl-1,3-benzenediamine, 4,6-diethyl-2-methyl-1,3-benzenediamine, 2,4-diisopropyl-6-methyl-1,3-benzenediamine, 2-methyl-4,6-di-sec-butyl-1,3-benzenediamine, 2-ethyl-4-isopropyl-6-methyl-1,3-benzenediamine, 2,3,5-tri-n-propyl-1,4-benzenediamine, 2,3-diethyl-5-sec-butyl-1,4-benzenediamine, 3,4-dimethyl-5,6-diheptyl-1,2-benzenediamine, 2,4,5,6-tetra-n-propyl-1,3-benzenediamine, 2,3,5,6-tetraethyl-1,4-benzenediamine, 2,2'-methylenebis(6-n-propylbenzeneamine), 2,2'-methylenebis(3,6-di-n-propylbenzeneamine), 3,3'-methylenebis(2,6-di-n-butylbenzeneamine), 4,4'-methylenebis(2,6-diethylbenzeneamine), 4,4'-methylenebis(2,6-diisopropylbenzeneamine), 4,4'-methylenebis(2-isopropyl-6-methylbenzeneamine), 4,4'-(1,2-ethanediyl)bis(2,6-diethylbenzeneamine), 4,4'-(1,2-ethanediyl)bis(2,6-diisopropylbenzeneamine), 2,2'-methylenebis(3,4,6-tripentylbenzeneamine), 3,3'-methylenebis(2,5,6-trihexylbenzeneamine), 4,4'-methylenebis(2,3,6-trimethylbenzeneamine), 4,4'-methylenebis(2,3,4,6-tetramethylbenzeneamine), and the like. Of these more preferred types of aromatic primary diamines, particularly preferred are 4,4'-methylenebis(2,6-diethylbenzeneamine), 4,4'-methylenebis(2,6-diisopropylbenzeneamine), and a mixture of 2,4-diethyl-6-methyl-1,3-benzenediamine and 4,6-diethyl-2-methyl-1,3-benzenediamine (DETDA, Ethacure® 100).

Those of skill in the art will recognize that there are several ways to name the aromatic primary diamines used in this invention. For example, the structure

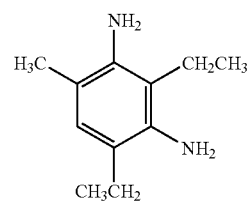

which represents a particularly preferred aromatic primary diamine in this invention, can be called 2,4-diethyl-6-methyl-1,3-benzenediamine, 2,4-diethyl-6-methyl-1,3-phenylenediamine, 3,5-diethyl-2,4-diaminotoluene, or 3,5-diethyl-toluene-2,4-diamine. Similarly, the structure

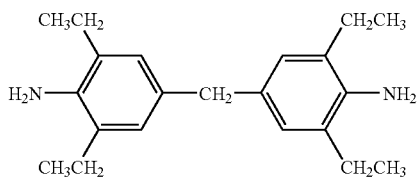

which represents another particularly preferred aromatic primary diamine in this invention, can be called 4,4'-methylenbis(2,6-diethylbenzeneamine), 4,4'-methylenbis(2,6-diethylaniline), or 3,3',5,5'-tetraethyl-4,4'-diaminodiphenylmethane.

II. Component (ii)

Component (ii) is selected from the group consisting of (a) an aliphatic secondary diamine; (b) an aliphatic primary diamine; (c) an aliphatic secondary diamine and an aliphatic primary diamine; (d) a diimine; and (e) a combination of any two or more of (a) through (d). When (ii) is (a), (a) has amino hydrocarbyl groups which are secondary or tertiary hydrocarbyl groups. When (ii) is (d), and (d) is an aromatic diimine, each imino hydrocarbylidene group has at least two carbon atoms. Thus mixtures of subcomponents (a)-(d) in various combinations are within the scope of this invention.

Subcomponent (a)

Aliphatic secondary diamines which have amino hydrocarbyl groups which are secondary or tertiary hydrocarbyl groups are subcomponent (a) of component (ii). The amino hydrocarbyl groups of the aliphatic secondary diamine can be cyclic or branched. Preferably, the amino hydrocarbyl groups are branched chain alkyl groups having from three to about twelve carbon atoms. Examples of suitable amino hydrocarbyl groups include isopropyl, sec-butyl, t-butyl, 3,3-dimethyl-2-butyl, 3-pentyl, cyclopentyl, 4-hexyl, methylcyclohexyl, cyclooctyl, 5-nonyl, and the like.

The aliphatic secondary diamines are hydrocarbyl secondary diamines where the hydrocarbyl portion of the diamine is aliphatic, where "hydrocarbyl portion" refers to the moiety to which the amino groups are bound. The hydrocarbyl portion of the aliphatic diamine can be cyclic, branched, or straight chain. Cyclic and straight chain are preferred as the hydrocarbyl portion of the aliphatic secondary diamine. When the hydrocarbyl portion of the diamine is cyclic, the cyclic moiety can be a single ring, fused rings, bicyclic rings, or a tricyclic system (which tricyclic system can contain fused rings and/or bicyclic rings). The amino groups may be attached directly to the ring, or one or both amino groups may be bound to a group that is a substituent of the ring; it is preferred that at least one of the amino groups is bound to the ring. Preferably, the aliphatic secondary diamine has about twelve to about forty carbon atoms; more preferably, the aliphatic secondary diamine has about fifteen to about twenty-five carbon atoms. The relative proportions of aromatic primary diamine to aliphatic secondary diamine in the chain extender composition are preferably about 0.5:1 to about 1:0.5 on an equivalent basis; more preferably, the relative proportions on an equivalent basis are about 0.75:1 to about 1:0.75. On a weight basis, the relative proportions of aromatic primary diamine to aliphatic secondary diamine in the chain extender composition are preferably about 0.25:1 to about 5:1; more preferably, the relative proportions on a weight basis are about 0.5:1 to about 3:1.

A preferred chain extender composition, when component (ii) is an aliphatic secondary diamine which has amino hydrocarbyl groups which are secondary or tertiary hydrocarbyl groups, in which the hydrocarbyl portion of the aliphatic secondary diamine is a straight chain, has relative proportions of (i) to (ii) on a weight basis of about 0.25:1 to about 5:1.

Aliphatic secondary diamines that can be used in this invention include, but are not limited to, N,N'-diisopropylethylenediamine, N,N'-di-sec-butyl-1,2-diaminopropane, N,N'-di(1-cyclopropylethyl)-1,5-diaminopentane, N,N'-di(3,3-dimethyl-2-butyl)-1,5-diamino-2-methylpentane, N,N'-di-sec-butyl-1,6-diaminohexane, N,N'-di(3-pentyl)-2,5-dimethyl-2,5-hexanediamine, N,N'-di(4-hexyl)-1,2-diaminocyclohexane, N,N'-dicyclohexyl-1,3-diaminocyclohexane, N,N'-di(1-cyclobutylethyl)-1,4-diaminocyclohexane, N,N'-di(2,4-dimethyl-3-pentyl)-1,3-cyclohexanebis(methylamine), N,N'-diisopropyl-1,7-diaminoheptane, N,N'-di-sec-butyl-1,8-diaminooctane, N,N'-di(2-pentyl)-1,10-diaminodecane, N,N'-di(3-hexyl)-1,12-diaminododecane, N,N'-di(3-methyl-2-cyclohexenyl)-1,2-diaminopropane, N,N'-di(2,5-dimethylcyclopentyl)-1,4-diaminobutane, N,N'-di(isophoryl)-1,5-diaminopentane, N,N'-di(menthyl)-2,5-dimethyl-2,5-hexanediamine, N,N'-di(5-nonyl)-isophoronediamine, and N,N'-di-(3,3-dimethyl-2-butyl)-3(4),8(9)-bis-(aminomethyl)-tricyclo[5.2.1.0(2,6)] decane (also called N,N'-di-(3,3-dimethyl-2-butyl)-TCD diamine). Preferred aliphatic secondary diamines include N,N'-di-(3,3-dimethyl-2-butyl)-1,6-diaminohexane, N,N'-di-2-(4-methylpentyl)-isophoronediamine, and N,N'-di-(3,3-dimethyl-2-butyl)-TCD diamine.

Subcomponent (b)

Aliphatic primary diamines are subcomponent (b) of component (ii), and the aliphatic primary diamines used in this invention are hydrocarbyl primary diamines where the hydrocarbyl portion of the diamine is aliphatic. The hydrocarbyl portion of the aliphatic diamine can be cyclic, branched, or straight chain. Preferably, the aliphatic primary diamine has about two to about twenty carbon atoms; more preferably, the aliphatic primary diamine has about four to about twelve carbon atoms. Particularly preferred aliphatic diamines have cyclic or straight chain hydrocarbyl portions and have about four to about ten carbon atoms.

Suitable aliphatic primary diamines include, but are not limited to, ethylenediamine, 1,2-diaminopropane, 1,3-diaminopropane, 1,4-diaminobutane, 1,5-diaminopentane, 1,5-diamino-2-methylpentane, 1,6-diaminohexane, 2,5-dimethyl-2,5-hexanediamine, 1,2-diaminocyclohexane, 1,3-diaminocyclohexane, 1,4-diaminocyclohexane, 2,4-diethyl-6-methyl-1,3-cyclohexanediamine, 4,6-diethyl-2-methyl-1,3-cyclohexanediamine, 1,3-cyclohexanebis(methylamine), 1,4-cyclohexanebis(methylamine), isophorone diamine, bis (p-aminocyclohexyl)methane, bis(3-methyl-4-aminocyclohexyl)methane, 1,8-diamino-p-menthane, 1,7-diaminoheptane, 1,8-diaminooctane, 1,10-diaminodecane, 1,12-diaminododecane, and 3(4),8(9)-bis-(aminomethyl)-tricyclo [5.2.1.0(2,6)]decane (TCD diamine; also called octahydro-4,7-methanoinden-1(2),5(6)-dimethanamine or octahydro-4,7-methano-1H-indenedimethyl-amine). Preferred aliphatic primary diamines include isophorone diamine and TCD diamine.

Subcomponent (c)

An aliphatic secondary diamine and an aliphatic primary diamine are subcomponent (c) of (ii). The aliphatic secondary diamine and the aliphatic primary diamine can be in any suitable proportion relative to each other, and their combined total amount can be in any relative proportion to the aromatic primary diamine of (i). Preferably, the proportion of the combined total amount of aliphatic secondary diamine and aliphatic primary diamine relative to the aromatic primary diamine of (i) is in the range of about 0.5:1 to about 1:0.5.

Suitable aliphatic primary diamines for subcomponent (c) and preferences therefor are as described above for subcomponent (b). Similarly, when the aliphatic secondary diamine of subcomponent (c) has secondary or tertiary amino hydrocarbyl groups, suitable aliphatic secondary diamines and preferences therefor are as described above for subcomponent (a). When the aliphatic secondary diamine of subcomponent (c) is an aliphatic secondary diamine in which the amino hydrocarbyl groups are primary, the hydrocarbyl portion of the aliphatic diamine can be branched, or, preferably, straight chain or cyclic. The amino hydrocarbyl groups of the aliphatic secondary diamine can be cyclic, branched, or straight chain. Preferably, the amino hydrocarbyl groups are straight chain or, more preferably, branched chain alkyl groups having from three to about twelve carbon atoms. Examples of suitable amino hydrocarbyl groups include ethyl, propyl, n-butyl, pentyl, hexyl, heptyl, octyl, nonyl, decyl, dodecyl, and the like. Preferred aliphatic secondary diamines with primary amino hydrocarbyl groups have cyclic or straight chain hydrocarbyl portions and have about twelve to about twenty-five carbon atoms.

Examples of aliphatic secondary diamines having primary amino hydrocarbyl groups that can be used in this invention are N,N'-didodecylethylenediamine, N,N'-didecyl-1,3-diaminopropane, N,N'-dinonyl-1,5-diaminopentane, N,N'-diheptyl-1,5-diamino-2-methylpentane, N,N'-di-n-butyl-1,6-diaminohexane, N,N'-di-n-propyl)-2,5-dimethyl-2,5-hexanediamine, N,N'-dihexyl-1,2-diaminocyclohexane, N,N'-didecyl-1,3-diaminocyclohexane, N,N'-di-n-butyl-1,4-diaminocyclohexane, N,N'-dipentyl-1,3-cyclohexanebis(methylamine), N,N'-dinonyl-1,4-cyclohexanebis(methylamine), N,N'-di-n-propyl-1,7-diaminoheptane, N,N'-di-n-butyl-1,8-diaminooctane, N,N'-dipenty-1,10-diaminodecane, N,N'-dihexyl-1,12-diaminododecane, N,N'-di(undecyl)-1,2-diaminocyclohexane, N,N'-dihexylisophoronediamine, N,N'-dioctyl)-isophoronediamine, N,N'-dipentyl-TCD diamine, and the like.

Subcomponent (d)

Diimines (which are also called diketimines) are subcomponent (d) of component (ii). Processes for forming diimines from primary diamines are provided in commonly-owned copending U.S. patent application Ser. No. 11/390,777, filed Mar. 27, 2006, and PCT Application No. PCT/US 2005/47696, filed Dec. 30,2005. Other disclosures of methods for making diimines include WO 97/01529, and U.S. Pat. Nos. 4,855,500, and 4,536,518.

Aromatic diimines suitable for use in this invention can be represented by the structures:

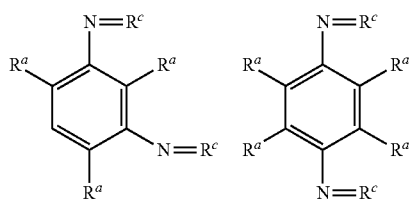

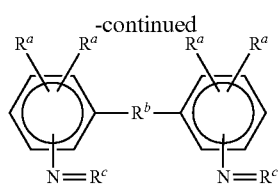

where each $R^a$ may be the same or different, and each $R^a$ is a hydrocarbyl group, $R^b$ is an alkylene bridge, and each $R^c$ is a hydrocarbylidene group having at least two carbon atoms.

Aromatic diimines that can be used in this invention are aromatic diimines in which the imino hydrocarbylidene groups have at least two carbon atoms. One type of aromatic diimine that can be used in this invention is either in the form of one phenyl ring having two imino groups on the ring, in which each position ortho to an imino group (—N═R) bears a hydrocarbyl group, or in the form of two phenyl rings connected by an alkylene bridge and having one imino group on each ring, in which each position ortho to an imino group bears a hydrocarbyl group. Another type of aromatic diimine that can be used in this invention is an aromatic diimine in which at least one position ortho to each imino group has a hydrogen atom as a substituent, and which aromatic diimine is either in the form of one phenyl ring having two imino groups on the ring or in the form of two phenyl rings connected by an alkylene bridge and having one imino group on each ring.

The hydrocarbyl groups on the phenyl rings may be the same or different. Examples of suitable hydrocarbyl groups on the aromatic ring include methyl, ethyl, propyl, isopropyl, n-butyl, sec-butyl, t-butyl, pentyl, cyclopentyl, hexyl, methylcyclohexyl, heptyl, octyl, cyclooctyl, nonyl, decyl, dodecyl, phenyl, benzyl, and the like. When the aromatic diimine is in the form of two phenyl rings connected by an alkylene bridge and having one imino group on each ring and the imino group is adjacent (ortho) to the alkylene bridge, the alkylene bridge is considered as a hydrocarbyl group ortho to the imino group. Preferred hydrocarbyl groups on the phenyl ring(s) (ortho to an imino group) of the aromatic diimines are straight-chain or branched-chain alkyl groups having from one to about six carbon atoms; particularly preferred hydrocarbyl groups are methyl, ethyl, isopropyl, butyl, and mixtures of two or more of these groups. Here, the preference for butyl groups includes n-butyl, sec-butyl, and t-butyl groups. The alkylene bridge of the two-ringed diimine has from one to about six carbon atoms; preferably, the bridge has from one to about three carbon atoms. More preferably, the alkylene bridge has one or two carbon atoms; highly preferred is an alkylene bridge having one carbon atom, i.e., a methylene group.

The hydrocarbylidene groups of the imino groups of the aromatic diimine generally have from two to about twenty carbon atoms; the hydrocarbylidene groups may be aliphatic (straight chain, branched, or cyclic) or aromatic. Preferably, the imino hydrocarbylidene groups are straight chain or branched chain alkylidene groups having from three to about six carbon atoms. Examples of suitable imino hydrocarbylidene groups include ethylidene, propylidene, isopropylidene, 1-cyclopropylethylidene, n-butylidene, sec-butylidene, cyclobutylidene, 2-ethylbutylidene, 3,3-dimethyl-2-butylidene, 3-pentylidene, 3-penten-2-ylidene, cyclopentylidene, 2,5-dimethylcyclopentylidene, 2-cyclopentenylidene, hexylidene, methylcyclohexylidene, menthylidene, ionylidene, phorylidene, isophorylidene, heptylidene, 2,6,-dimethyl-3-heptylidene, cyclooctylidene, 5-nonylidene, decylidene, 10-undecenylidene, benzylidene, 2,4-dimethylbenzylidene, 2-phenylethylidene, 1-phenylpentylidene, 1-naphthylidene, 2-naphthylidene, 1-naphthylethylidene, and the like.

Preferred aromatic diimines with two imino groups on one phenyl ring have the imino groups meta relative to each other. In these preferred diimines, the imino hydrocarbylidene group preferably is a straight chain or branched chain alkylidene group having from three to about six carbon atoms. Particularly preferred are aromatic diimines in which the hydrocarbyl group between the two meta imino groups is a methyl group, while the two remaining hydrocarbyl groups are ethyl groups, and those in which the hydrocarbyl group between the two meta imino groups is an ethyl group, while one of the two remaining hydrocarbyl groups is a methyl group and the other is an ethyl group, and mixtures thereof.

Preferred aromatic diimines in which one imino group is on each of two phenyl rings, where the two phenyl rings are connected via an alkylene bridge, have both imino groups para relative to the alkylene bridge. A particularly preferred aromatic diimine of this type is a compound where each hydrocarbyl group ortho to an imino group is an ethyl group and the alkylene bridge is a methylene group; this is especially preferred when the imino hydrocarbylidene groups are isopropylidene or sec-butylidene.

Diimines having both imino groups on one phenyl ring suitable for use in this invention include, but are not limited to, N,N'-diisopropylidene-2,4,6-triethyl-1,3-benzenediamine, N,N'-di-sec-butylidene-2,4,6-triethyl-1,3-benzenediamine, N,N'-di(2-pentylidene)-(2,4,6-triethyl-1,3-benzenediamine), N,N'-diisopropylidene-(2,4-diethyl-6-methyl-1,3-benzenediamine), N,N'-di-sec-butylidene-(2,4-diethyl-6-methyl-1,3-benzenediamine), N,N'-diisopropylidene-(4,6-diethyl-2-methyl-1,3-benzenediamine), N,N'-di-sec-butylidene-(4,6-diethyl-2-methyl-1,3-benzenediamine), N,N'-dicyclobutylidene-(4,6-diethyl-2-methyl-1,3-benzenediamine), N,N'-dicyclopentylidene-(2,4-diisopropyl-6-methyl-1,3-benzenediamine), N,N'-diisopropylidene-(2-methyl-4,6-di-sec-butyl-1,3-benzenediamine), N,N'-di(1-cyclopropylethylidene)-(2-methyl-4,6-di-sec-butyl-1,3-benzenediamine), N,N'-di(3,3-dimethyl-2-butylidene)-(2-ethyl-4-isopropyl-6-methyl-1,3-benzenediamine), N,N'-di(2-butenylidene)-2,4,5,6-tetra-n-propyl-1,3-benzenediamine, N,N'-di-sec-butylidene-2,3,5,6-tetraethyl-1,4-benzenediamine, and N,N'-di(2-phenylethylidene)-2,3,5,6-tetraethyl-1,4-benzenediamine.

Examples of aromatic diimines in which one imino group is on each of two phenyl rings suitable for use in this invention include N,N'-diisopropylidene-2,2'-methylenebis(6-n-propylbenzeneamine), N,N'-di-sec-butylidene-2,2'-methylenebis(6-n-propylbenzeneamine), N,N'-di-sec-butylidene-2,2'-methylenebis(3,6-di-n-propylbenzeneamine), N,N'-di(1-cyclobutylethylidene)-2,2'-methylenebis(5,6-dihexylbenzeneamine), N,N'-diisopropylidene-3,3'-methylenebis(2,6-di-n-butylbenzeneamine), N,N'-di(2,4-dimethyl-3-pentylidene)-3,3'-methylenebis(2,6-di-n-butylbenzeneamine), N,N'-diisopropylidene-4,4'-methylenebis(2,6-diethylbenzeneamine), N,N'-di-sec-butylidene-4,4'-methylenebis(2,6-diethylbenzeneamine), N,N'-di(benzylidene)-4,4'-methylenebis(2,6-diethylbenzeneamine), N,N'-di(2-heptylidene)-4,4'-methylenebis(2,6-diisopropylbenzeneamine), N,N'-dicyclobutylidene-4,4'-methylenebis(2-isopropyl-6-methylbenzeneamine), N,N'-di(3-methyl-2-cyclohexenylidene)-4,4'-methylenebis(2-methyl-6-tert-butylbenzeneamine), N,N'-di-sec-butylidene-4,4'-(1,2-ethanediyl)bis(2,6-diethylbenzeneamine), N,N'-di(1-cyclopentylethylidene)-4,4'-(1,2-ethanediyl)bis(2,6-diethylbenzeneamine), N,N'-di(1-phenyl-2-butylidene)-4,4'-(1,2-ethanediyl)bis(2,6-diisopropylbenzeneamine), N,N'-di(2-phenylethylidene)-2,2'-methylenebis(3,4,6-tripentylbenzeneamine), N,N'-di(4-heptylidene)-3,3'-methylenebis(2,5,6-trihexylbenzeneamine), N,N'-dicyclohexylidene-4,4'-methylenebis(2,3,6-trimethylbenzeneamine), N,N'-di(1-cyclobutylethylidene)-4,4'-methylenebis(2,3,4,6-tetramethylbenzeneamine), and the like.

Other aromatic diimines which can be employed in this invention include, but are not limited to, N,N'-diisopropylidene-1,2-benzenediamine, N,N'-di-sec-butylidene-1,3-benzenediamine, N,N'-di(3-hexylidene)-1,4-benzenediamine, N,N'-dicyclopentylidene-4-ethyl-1,2-benzenediamine, N,N'-di-sec-butylidene-(4-tert-butyl-1,3-benzenediamine), N,N'-di(1-cyclopropylethylidene)-2-pentyl-1,4-benzenediamine, N,N'-di(undecylidene)-(4-methyl-5-heptyl-1,3-benzenediamine), N,N'-di(2-cyclopentenylidene)-4,6-di-n-propyl-1,3-benzenediamine, N,N'-di-sec-butylidene-2,3-diethyl-1,4-benzenediamine, N,N'-di(2-butenylidene)-4,5,6-trihexyl-1,3-benzenediamine, N,N'-di(2,5-dimethylcyclopentylidene)-2,2'-methylenebis(benzeneamine), N,N'-dimenthylidene-2,3'-methylenebis(benzeneamine), N,N'-diisopropylidene-2,4'-methylenebis(benzeneamine), N,N'-di-sec-butylidene-3,3'-methylenebis(benzeneamine), N,N'-di(3-methyl-2-cyclohexenylidene)-3,4'-methylenebis(benzeneamine), N,N'-di(3,3-dimethyl-2-butylidene)-4,4'-methylenebis(benzeneamine), N,N'-di(3-pentylidene)-4,4'-(1,2-ethanediyl)bisbenzeneamine, N,N'-di(undecylidene)-3,4'-(1,3-propanediyl)bis(benzeneamine), N,N'-di(2,4-dimethyl-3-pentylidene)-2,2'-methylenebis(5-tert-butylbenzeneamine), N,N'-di(phorylidene)-3,3'-methylenebis(5-pentylbenzeneamine), N,N'-di(3-methylbutylidene)-3,3'-methylenebis(6-isopropylbenzeneamine), N,N'-di(2-heptylidene)-4,4'-methylenebis(2-methylbenzeneamine), N,N'-dimenthylidene-4,4'-methylenebis(3-sec-butylbenzeneamine), N,N'-di(1-cyclopentylethylidene)-4,4'-(1,2-ethanediyl)bis(2-methylbenzeneamine), and N,N'-di(1-penten-3-ylidene)-4,4'-methylenebis(2,3-di-sec-butylbenzeneamine).

Aliphatic diimines are also part of subcomponent (d) of the curative mixture. The hydrocarbyl portion of the aliphatic diimine can be cyclic, branched, or straight chain hydrocarbyl group, where "hydrocarbyl portion" refers to the moiety to which the imino groups are bound. Preferably, the aliphatic diimine has about six to about forty carbon atoms; more preferably, the aliphatic diimine has about ten to about thirty carbon atoms. The hydrocarbylidene groups of the imino groups of the aliphatic diimine generally have from one to about twenty carbon atoms; the hydrocarbylidene groups may be straight chain, branched, or cyclic. Preferably, the imino hydrocarbylidene groups are straight chain or branched chain alkylidene groups having from three to about six carbon atoms. Examples of suitable imino hydrocarbylidene groups include ethylidene, propylidene, isopropylidene, 1-cyclopropylethylidene, n-butylidene, sec-butylidene, cyclobutylidene, 2-ethylbutylidene, 3,3-dimethyl-2-butylidene, 3-pentylidene, 3-penten-2-ylidene, cyclopentylidene, 2,5-dimethylcyclopentylidene, 2-cyclopentenylidene, hexylidene, methylcyclohexylidene, menthylidene, ionylidene, phorylidene, isophorylidene, heptylidene, 2,6,-dimethyl-3-heptylidene, cyclooctylidene, 5-nonylidene, decylidene, 10-undecenylidene, and the like.

Aliphatic diimines that can be used in this invention include, but are not limited to, N,N'-diisopropylidene-ethylenediamine, N,N'-di-sec-butylidene-1,2-diaminopropane, N,N'-di(2-butenylidene)-1,3-diaminopropane, N,N'-di(1-cyclopropylethylidene)-1,5-diaminopentane,N,N'-di(3,3-dimethyl-2-butylidene)-1,5-diamino-2-methylpentane, N,N'-disec-butylidene-1,6-diaminohexane, N,N'-di(3-pentylidene)-2,5-dimethyl-2,5-hexanediamine, N,N'-di(4-hexylidene)-1,2-diaminocyclohexane, N,N'-dicyclohexylidene-1,3-diaminocyclohexane, N,N'-di(1-cyclobutylethylidene)-1,4-diaminocyclohexane, N,N'-di(2,4-dimethyl-3-pentylidene)-1,3-cyclohexanebis(methylamine), N,N'-di(1-penten-3-ylidene)-1,4-cyclohexanebis(methylamine), N,N'-diisopropylidene-1,7-diaminoheptane, N,N'-di-sec-butylidene-1,8-diaminooctane, N,N'-di(2-pentylidene)-1,10-diaminodecane, N,N'-di(3-hexylidene)-1,12-diaminododecane, N,N'-di(3-methyl-2-cyclohexenylidene)-1,2-diaminopropane, N,N'-di(2,5-dimethylcyclopentylidene)-1,4-diaminobutane, N,N'-di(isophorylidene)-1,5-diaminopentane, N,N'-di(menthylidene)-2,5-dimethyl-2,5-hexanediamine, N,N'-di(undecylidene)-1,2-diaminocyclohexane, N,N'-di-2-(4-methylpentylidene)-isophoronediamine, and N,N'-di(5-nonylidene)-isophoronediamine.

Processes of the Invention

In the processes of the invention, a polymer which is a polyurethane, polyurea, or polyurea-urethane is made by mixing together at least one aromatic isocyanate, at least one polyol and/or at least one polyetheramine, and a chain extender composition of the invention. As is well known in the art, other components may also be included when making the polyurethane, polyurea, or polyurethane-urea, such as one or more flame retardants, thermal stabilizers, and/or surfactants. In some processes of the invention, the polyol or polyetheramine, chain extender composition, and when used, optional ingredients, are blended together to form a first mixture, followed by blending this first mixture with the isocyanate to form a second mixture; this second mixture is allowed to cure. In other processes of this invention, the isocyanate and the polyol or polyetheramine are blended together to form a prepolymer, which prepolymer is then mixed together with the chain extender composition to form the desired polymer. In still other processes of the invention, the isocyanate is mixed with polyol or polyetheramine to form a quasiprepolymer; polyol or polyetheramine is mixed with the chain extender composition to form a mixture; and then the mixture is mixed with the quasiprepolymer to form the desired polymer. Thus, the chain extender composition is reacted with an aromatic polyisocyanate and at least one polyol and/or at least one polyetheramine or with a prepolymer or a quasiprepolymer of the isocyanate and the polyol or polyetheramine. In the practice of this invention, use of quasiprepolymers is preferred way of producing polyureas.

The aromatic polyisocyanates are organic polyisocyanates having at least two isocyanate groups. Generally, the isocyanates have a free —NCO content of at least about 0.1% by weight. Aromatic polyisocyanates that can be used in the practice of this invention include phenylene diisocyanate, toluene diisocyanate (TDI), xylene diisocyanate, 1,5-naphthalene diisocyanate, chlorophenylene 2,4-diisocyanate, bitoluene diisocyanate, dianisidine diisocyanate, tolidine diisocyanate, alkylated benzene diisocyanates, methylene-interrupted aromatic diisocyanates such as methylenediphenyl diisocyanates, especially 4,4-methylenediphenyl diisocyanate (MDI), alkylated analogs of methylene-interrupted aromatic diisocyanates (such as 3,3'-dimethyl-4,4'-diphenylmethane diisocyanate), and polymeric methylenediphenyl diisocyanates. A preferred aromatic polyisocyanate is 4,4-methylenediphenyl diisocyanate (MDI). Examples of isocyanates that can be used are also taught in, for example, U.S. Pat. No. 4,595,742.

Isocyanate-reactive polyols and polyetheramines (sometimes referred to as amine-terminated polyols) that are typically used in making polyurethanes, polyureas, and polyurea-urethanes range in molecular weight from about 60 to over 6,000. The polyols can be dihydric, trihydridic, or polyhydric polyols, but are usually dihydric. Examples of suitable polyols include poly(ethyleneoxy) glycols, dipropylene glycol, poly(propyleneoxy) glycols, dibutylene glycol, poly(butyleneoxy) glycols, and the polymeric glycol from caprolactone, commonly known as polycaprolactone. The polyetheramines used to make polyurethanes, polyureas, and polyurea-urethanes are amine-capped polyols which are the reaction product of a polyol and then an amine with alkylene oxides as well as amine-capped hydroxyl-containing polyesters. Polyetheramines typically have a molecular weight of about 200 to about 6000. Several commercially available polyetheramines known as Jeffamines® available from Huntsman Chemical Company and include Jeffamine® T-5000, a polypropylene oxide triamine of about 5000 molecular weight, XTJ-509, a polypropylene oxide triamine of about 3000 molecular weight, XTJ-510, a polypropylene oxide diamine of about 4000 molecular weight, and Jeffamine® D-2000, a polypropylene oxide diamine of about 2000 molecular weight. Jeffamine® T-5000 and Jeffamine® D-2000 are preferred polyetheramines in the practice of this invention.

In a preferred process of the invention, the polyisocyanate is 4,4-methylenediphenyl diisocyanate. In another preferred process of the invention, at least one polyetheramine is used. In still another preferred process of the invention, component (i) of the chain extender composition is aromatic primary diamine in which each position ortho to an amino group bears a hydrocarbyl group, and which aromatic primary diamine is in the form of one phenyl ring having two amino groups on the ring, which amino groups are meta or para relative to each other, and in which the aromatic primary diamine has amino groups are meta relative to each other, and/or the ortho hydrocarbyl groups are methyl, ethyl, isopropyl, butyl, or mixtures thereof.

Polymers Formed by the Invention

The polymers formed by the invention are polyurethanes, polyureas, and polyurea-urethanes (sometimes called polyurea-polyurethanes). Because of their differing gel times (cure rates), these polymers can be used in different applications. Polyurethanes, polyureas, and polyurea-urethanes made with the chain extender compositions of the invention have more desirable gel times, and, at a minimum, the physical properties of the polymers are not adversely affected by the use of the chain extender compositions of the invention. In fact, an improvement in the tensile strength of the polymers made from chain extender compositions of the invention is observed in comparison to polymers made with the individual chain extenders.

A preferred polymer formed by this invention is formed from 4,4-methylenediphenyl diisocyanate; another preferred polymer formed by this invention is formed from at least one polyetheramine. Another preferred polymer formed by this invention is formed from a chain extender composition of the invention in which component (i) is an aromatic primary diamine in which each position ortho to an amino group bears a hydrocarbyl group, and which aromatic primary diamine is in the form of one phenyl ring having two amino groups on the ring, which amino groups are meta or para relative to each other, and in which the amino groups of the aromatic primary diamine are meta relative to each other and/or the ortho hydrocarbyl groups of the aromatic primary diamine are methyl, ethyl, isopropyl, butyl, or mixtures thereof.

Still another preferred polymer formed by this invention is formed from isophorone diisocyanate, at least one polyetheramine, and a chain extender composition in which component (ii) is an aliphatic secondary diamine and an aliphatic primary diamine, and in which the aliphatic secondary diamine is N,N'-di-(3,3-dimethyl-2-butyl)-1,6-diaminohexane, N,N'-di-2-(4-methylpentyl)-isophoronediamine, or N,N'-di-(3,3-dimethyl-2-butyl)-3(4),8(9)-bis-(aminomethyl)-tricyclo[5.2.1.0(2,6)]decane.

The following examples are presented for purposes of illustration, and are not intended to impose limitations on the scope of this invention.

EXAMPLE 1

In this example, the isocyanate was 4,4-methylenediphenyl diisocyanate (MDI, 15.2% NCO, Rubinate® 9480, Huntsman Chemical). Jeffamine® D-2000 and Jeffamine® T-5000 (polyetheramines, Huntsman Chemical) were used to make the polyureas, with the Jeffamine® D-2000 and Jeffamine® T-5000 in a 0.92:0.08 weight ratio. The aromatic primary diamine was a mixture of 2,4-diethyl-6-methyl-1,3-benzenediamine and 4,6-diethyl-2-methyl-1,3-benzenediamine (Ethacure® 100, Albemarle Corporation). A pneumatic dispensing gun (DP-400-85-1, Mixpac Systems AG, Switzerland) was used in conjunction with a static mixer. The static mixer was either a plastic spiral bell mixer with 30 elements and an inner diameter of 0.37 inches (EA 370-30, Ellsworth Adhesives) or a plastic bell mixer with 48 elements and an inner diameter of 0.25 inches (Statomix® MS 06-48).

Polyurea formulations containing isocyanate, Jeffamine® D-2000 and Jeffamine® T-5000, Ethacure® 100, and an aliphatic secondary diamine were prepared. The Ethacure® 100 and the aliphatic secondary diamine were used in a 1:1 ratio by equivalents. The isocyanate was mixed together with a portion of the Jeffamines® to form a quasiprepolymer. The remainder of the Jeffamines® was blended with the chain extender(s) to form a mixture. This mixture was then added to one compartment of the pneumatic mixing gun; the quasiprepolymer was added to the other compartment. The mixture and quasiprepolymer were mixed (reacted) by pushing them through a static mixer onto a steel plate and cured at room temperature. One polyurea was prepared without an aliphatic secondary diamine for comparative purposes. Amounts of the chain extenders relative to each other (in equivalents) are listed in Table 1. The cured polymers were subjected to testing. Properties of the polyureas are summarized in Table 1.

TABLE 1

| | Comparative | Run 1 | Run 2 | Run 3 |
|---|---|---|---|---|
| Ethacure ® 100 | 1 | 1 | 1 | 1 |
| N,N'-di-2-(4-methylpentyl)-isophoronediamine | 0 | 1 | 0 | 0 |
| N,N'-di-(3,3-dimethyl-2-butyl)-TCD diamine | 0 | 0 | 1 | 0 |
| N,N'-di-(3,3-dimethyl-2-butyl)-1,6-diaminohexane | 0 | 0 | 0 | 1 |
| Gel time (cure rate) | <2 sec | 97 sec | 50 sec | 32 sec |
| Shore D hardness, 0 sec. | 45 | 44 | 57 | 48 |
| Shore D hardness, 10 sec. | 40 | 38 | 55 | 44 |
| Tensile strength | 2310 psi | 2030 psi | 2410 psi | 2180 psi |
| Elongation, % | 370% | 370% | 280% | 380% |
| Modulus (100%) | 1300 psi | 990 psi | 1570 psi | 1350 psi |
| Modulus (300%) | 2030 psi | 1720 psi | — | 2050 psi |
| Tear strength | 460 pli | 470 pli | 630 pli | 530 pli |

EXAMPLE 2

Polyurea formulations were prepared as described in Example 1. The amounts of Jeffamine® D-2000 and Jeffamine® T-5000 were different than in Example 1. The chain extenders were Ethacure® 100, and N,N'-di-(3,3-dimethyl-2-butyl)-1,6-diaminohexane in various proportions. Ethacure® 100-LC (Albemarle Corporation) is Ethacure® 100 of lower color with a stabilizer present at ppm levels. Two polyureas were prepared for comparative purposes. Amounts of the chain extenders and Jeffamines® by weight are listed in Table 2. The cured polymers were subjected to testing. Properties of the polyureas are summarized in Table 2.

TABLE 2

| | Comparative | Run 1 | Run 2 | Run 3 | Run 4 | Comparative |
|---|---|---|---|---|---|---|
| Jeffamine ® D-2000 | | | | | 54.2 | |
| Jeffamine ® T-5000 | | | | | 5.4 | |
| Ethacure ® 100-LC | 0 | 0 | 0 | 0 | 15.6 | 0 |
| Ethacure ® 100 | 28.1 | 21.8 | 17.8 | 14.6 | 0 | 0 |
| N,N'-di-(3,3-dimethyl-2-butyl)-1,6-diaminohexane | 0 | 10.9 | 17.8 | 23.3 | 24.9 | 55.7 |
| Mix temperature | | | | | 58° C. | |
| Gel time (cure rate) | <2 sec | 6 sec | 10 sec | 16 sec | 16 sec | 49 sec |
| Shore D hardness, 0 sec. | 45 | 41 | 42 | 43 | 43 | 49 |
| Shore D hardness, 10 sec. | 40 | 38 | 38 | 39 | 39 | 44 |
| Tensile strength | 2310 psi | 2320 psi | 2530 psi | 2460 psi | 2410 psi | 2180 psi |
| Elongation | 370% | 350% | 390% | 360% | 350% | 330% |
| Modulus (100%) | 1300 psi | 1300 psi | 1320 psi | 1340 psi | 1390 psi | 1410 psi |
| Modulus (300%) | 2030 psi | 2120 psi | 2190 psi | 2230 psi | 2240 psi | 2120 psi |
| Tear strength | 460 pli | 430 pli | 450 pli | 470 pli | 460 pli | 510 pli |

EXAMPLE 3

Polyurea formulations containing isocyanate (MDI, 15.2% NCO, Rubinate® 9480, Huntsman Chemical), Jeffamine® D-2000, Jeffamine® T-5000, Ethacure® 100, and/or N,N'-di-(3,3-dimethyl-2-butyl)-TCD diamine were prepared; one formulation was prepared using only Ethacure® 100, for comparative purposes. All ingredients except the isocyanate were mixed together in a blender for five minutes and then degassed in an oven; amounts of the components in this mixture are listed in Table 3. The mixture was placed in one barrel of a two-barrel syringe; the isocyanate was placed in the other barrel. The syringe contents were blended by pushing them through a static mixer onto a steel plate and cured at room temperature. A 1:1 volume ratio of isocyanate to the mixture resulted from the blending of the syringe contents. The cured formulations were then subjected to testing. Amounts of the components in each formulation are listed in Table 3. The formulation having N,N'-di-(3,3-dimethyl-2-butyl)-TCD diamine without Ethacure® 100 was observed to be brittle. Properties of the formulations are summarized in Table 3.

TABLE 3

| Component | Formulation 1 | Formulation 2 | Formulation 3 |
|---|---|---|---|
| Amine-terminated polyol (Jeffamine ® D-2000) | 66.1 wt % | 49.5 wt % | 31.3 wt % |
| Amine-terminated polyol (Jeffamine ® T-5000) | 5.8 wt % | 5.8 wt % | 5.7 wt % |
| Ethacure ® 100 | 28.1 wt % | 14.7 wt % | 0 |
| Amount of diamine | 0 | 30.0 wt % | 63.0 wt % |
| Gel time (cure rate) | <2 sec. | 11 sec. | 50 sec. |
| Shore D hardness, 0 sec | 45 | 47 | 57 |
| Shore D hardness, 10 sec | 40 | 43 | 55 |
| Tensile strength | 2310 psi | 2500 psi | 2410 psi |
| Elongation | 370% | 360% | 280% |
| Modulus (100%) | 1300 psi | 1340 psi | 1570 psi |
| Modulus (300%) | 2030 psi | 2250 psi | 1790 psi |
| Tear strength | 460 pli | 500 pli | 630 pli |

Formulations similar to the those in Example 3 were made with N,N'-di-5-nonyl-isophoronediamine. The gel time (cure rate) for the N,N'-di-5-nonyl-isophoronediamine formulation was 59 seconds. Another formulation similar to those in Example 3 was made with N,N'-di-2-(4-methylpentyl)-isophoronediamine; the gel time for this formulation was 22 seconds. Still another formulation similar to those in Example 3 was made with N,N'-di-(3,3-dimethyl-2-butyl)-TCD diamine; the gel time for this formulation was 25 seconds. Yet another formulation similar to those in Example 3 was made with N,N'-di-(3,3-dimethyl-2-butyl)-1,6-diaminohexane; the gel time for this formulation was 25 seconds at room temperature.

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation in its practice.

The invention claimed is:

1. A chain extender composition which comprises
   (i) an aromatic primary diamine, and
   (ii) an aliphatic secondary diamine which is N,N'-di-(3,3-dimethyl-2-butyl)-1,6-diaminohexane, and an aliphatic primary diamine.

2. A composition as in claim 1 wherein (i) is an aromatic primary diamine in which each position ortho to an amino group bears a hydrocarbyl group, and which aromatic primary diamine is in the form of one phenyl ring having two amino groups on the ring, which amino groups are meta or para relative to each other.

3. A composition as in claim 1 wherein (i) is an aromatic primary diamine in which each position ortho to an amino group bears a hydrocarbyl group, and which aromatic primary diamine is in the form of two phenyl rings connected by an alkylene bridge and having one amino group on each ring.

4. A composition as in claim 1 wherein (i) is a mixture of 2,4-diethyl-6-methyl-1,3-benzenediamine and 4,6-diethyl-2-methyl-1,3-benzenediamine.

5. A composition as in claim 1 wherein said aliphatic primary diamine has at least one of the following features:
   the hydrocarbyl portion of the diamine is cyclic or a straight chain;
   the aliphatic primary diamine has about four to about ten carbon atoms.

* * * * *